(12) United States Patent
Callewaert

(10) Patent No.: US 12,226,503 B2
(45) Date of Patent: Feb. 18, 2025

(54) PREBIOTIC SKIN CARE COMPOSITIONS CONTAINING CARBOXYLIC ACIDS

(71) Applicant: Universiteit Gent, Ghent (BE)

(72) Inventor: Chris Callewaert, Ghent (BE)

(73) Assignee: Universiteit Gent, Ghent (BE)

( * ) Notice: Subject to any disclaimer, the term of this patent is extended or adjusted under 35 U.S.C. 154(b) by 653 days.

(21) Appl. No.: 17/605,418

(22) PCT Filed: Apr. 22, 2020

(86) PCT No.: PCT/EP2020/061119
§ 371 (c)(1),
(2) Date: Oct. 21, 2021

(87) PCT Pub. No.: WO2020/216757
PCT Pub. Date: Oct. 29, 2020

(65) Prior Publication Data
US 2022/0192949 A1   Jun. 23, 2022

(30) Foreign Application Priority Data
Apr. 25, 2019 (EP) .................................. 19171010

(51) Int. Cl.
*A61K 8/362* (2006.01)
*A61K 8/36* (2006.01)
(Continued)

(52) U.S. Cl.
CPC ................. *A61K 8/362* (2013.01); *A61K 8/36* (2013.01); *A61K 8/365* (2013.01); *A61K 8/368* (2013.01);
(Continued)

(58) Field of Classification Search
None
See application file for complete search history.

(56) References Cited

U.S. PATENT DOCUMENTS 6,162,422 A   12/2000 Casey et al.
6,171,582 B1   1/2001 Casey et al.
(Continued)

FOREIGN PATENT DOCUMENTS

DE   10333245 A1   7/2005
DE   102002012476 A1   9/2006
(Continued)

OTHER PUBLICATIONS

English translation for DE102005012476A1 (Year: 2006).*
(Continued)

*Primary Examiner* — Sin J Lee
(74) *Attorney, Agent, or Firm* — TraskBritt

(57) ABSTRACT

The disclosure relates to the field of reducing malodor, which is due to bacterial conversion of molecules that are present in sweat. Indeed, the disclosure describes acids, which steer the microbiome by inhibiting the growth of specific malodor-producing bacteria and/or promoting the growth of bacteria known to be beneficial in relation to malodor. The acids of the disclosure can thus be used in deodorants, washing powders, clothing finishing agents or any method to reduce malodor. The disclosure thus relates to a topical composition or textile finisher for use as a prebiotic.

17 Claims, 1 Drawing Sheet
Specification includes a Sequence Listing.

(51) Int. Cl.
A61K 8/365 (2006.01)
A61K 8/368 (2006.01)
A61K 8/44 (2006.01)
A61Q 15/00 (2006.01)

(52) U.S. Cl.
CPC .............. *A61K 8/44* (2013.01); *A61Q 15/00* (2013.01); *A61K 2800/70* (2013.01); *A61K 2800/74* (2013.01); *A61K 2800/77* (2013.01)

(56) References Cited

U.S. PATENT DOCUMENTS

| | | | |
|---|---|---|---|
| 6,183,731 B1 | 2/2001 | Carey et al. | |
| 7,569,530 B1 | 8/2009 | Pan et al. | |
| 2011/0256082 A1* | 10/2011 | Klingman | A61K 8/365 424/65 |
| 2015/0202136 A1 | 7/2015 | Lanzalaco et al. | |
| 2016/0089395 A1 | 3/2016 | Kleinberg et al. | |
| 2021/0069088 A1* | 3/2021 | Jiang | A61Q 19/00 |

FOREIGN PATENT DOCUMENTS

| | | | | |
|---|---|---|---|---|
| DE | 102005029777 A1 | 1/2007 | | |
| EP | 1902754 B1 | 3/2008 | | |
| FR | 3040624 A1 | 7/2019 | | |
| GB | 2284762 A | 6/1995 | | |
| JP | 0622540 B2 | 3/1994 | | |
| JP | 2005-270453 A | 10/2005 | | |
| JP | 2017-008095 A | 1/2017 | | |
| WO | 00/01353 A1 | 1/2000 | | |
| WO | WO-2010039654 A2 * | 4/2010 | ............. | A61K 31/60 |
| WO | WO-2018111704 A1 * | 6/2018 | ............. | A61K 8/06 |
| WO | 2019/011551 A1 | 1/2019 | | |
| WO | 2020/052916 A1 | 3/2020 | | |

OTHER PUBLICATIONS

Boonme et al. "Antiperspirants and Deodorants?: Active Ingredients and Novel Formulations" Jan. 2010;(01):5-10.
Bouslimani et al. "The impact of skin care products on skin chemistry and microbiome dynamics" BMC Biology (2019) 17:47.
Callewaert et al. "Bacterial and odor profile of polyester and cotton clothes after a fitness session" Comm. Appl Biol Sci. 2013;78(1).
Callewaert et al. "Characterization of *Staphylococcus* and *Corynebacterium* Clusters in the Human Axillary Region" PLoS One. Aug. 12, 2013;8(8).
Callewaert et al. "Deodorants and antiperspirants affect the axillary bacterial community" Arch Dermatol Res. Sep. 19, 2014;306(8):701-10.
Chen et al. "Transport of bile acids, sulfated steroids, estradiol 17-beta-D-glucuronide, and leukotriene C4 by human multidrug resistance protein 8 (ABCC11)" Mol Pharmacol. Feb. 2005;67(2):545-57.
Decréau et al. "Production of malodorous steroids from androsta-5,16-dienes and androsta-4,16-dienes by Corynebacteria and other human axillary bacteria" J Steriod Biochem Mol Biol. Sep. 2003;87:327-36.
Hasegawa et al. "Identification of new odoriferous compounds in human axillary sweat" Chem Biodivers. 2004;1(12):2042-50.
International Search Report for International Application No. PCT/EP2020/061119, mailed Jul. 20, 2020, 4 pages.
International Written Opinion for International Application No. PCT/EP2020/061119, mailed Jul. 20, 2020, 6 pages.
James et al. "Fatty acid metabolism by cutaneous bacteria and its role in axillary malodour" World J Microbiol Biotechnol. World Journal of Microbiology & Biotechnology 20: 787-793 (Apr. 2004).
James et al. "Microbiological and biochemical origins of human axillary odour" FEMS Microbiol Ecol. 2013;83(3):527-540.
Natsch et al. "A broad diversity of volatile carboxylic acids, released by a bacterial aminoacylase from axilla secretions, as candidate molecules for the determination of human-body odor type" Chem Biodivers. 2006;3(1):1-20.
Natsch et al. "A specific bacterial aminoacylase cleaves odorant precursors secreted in the human axilla" vol. 278, No. 8, Issue of Feb. 21, 2003, pp. 5718-5727.
Natsch et al. "Identification of odoriferous sulfanylalkanols in human axilla secretions and their formation through cleavage of cysteine precursors by a C-S lyase isolated from axilla bacteria" Chem Biodivers. 2004;1(7):1058-72.
Troccaz et al. "3-methyl-3-sulfanylhexan-1-ol as a major descriptor for the human axilla-sweat odour profile" Chem Biodivers. 2004;1(7):1022-35.
Troccaz et al. "Gender-Specific Differences between the Concentrations of Nonvolatile (R)/(S)-3-Methyl-3-Sulfanylhexan-1-Ol and (R)/(S)-3-Hydroxy-3-Methyl-Hexanoic Acid Odor Precursors in Axillary Secretions" Chem. Senses 34: 203-210, Jan. 2009.
Zeng et al. "Analysis of characteristic odors from human male axillae" J Chem Ecol. 17(7):1469-92 (Mar. 1991).

* cited by examiner

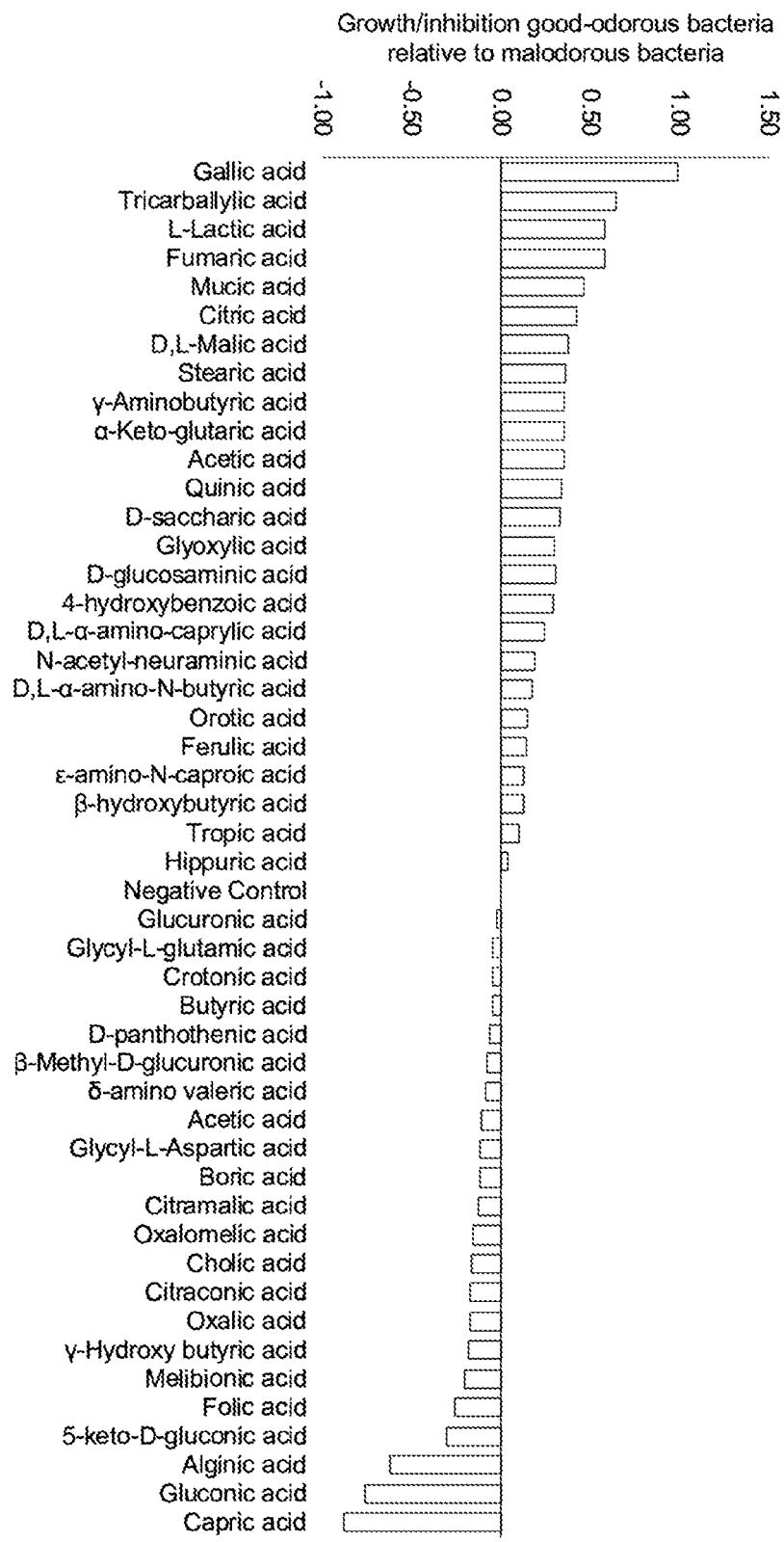

SEQUENCE LISTING

```
<160> NUMBER OF SEQ ID NOS: 9

<210> SEQ ID NO 1
<211> LENGTH: 1111
<212> TYPE: DNA
<213> ORGANISM: Staphylococcus epidermidis

<400> SEQUENCE: 1
tcctctgacg ttagcggcgg acgggtgagt aacacgtgga taacctacct ataagactgg      60
gataacttcg ggaaaccgga gctaataccg gataatatat tgaaccgcat ggttcaatag     120
tgaaagacgg ttttgctgtc acttatagat ggatccgcgc cgcattagct agttggtaag     180
gtaacggctt accaaggcaa cgatgcgtag ccgacctgag agggtgatcg gccacactgg     240
aactgagaca cggtccagac tcctacggga ggcagcagta gggaatcttc cgcaatgggc     300
gaaagcctga cggagcaacg ccgcgtgagt gatgaaggtc ttcggatcgt aaaactctgt     360
tattagggaa gaacaaatgt gtaagtaact atgcacgtct tgacggtacc taatcagaaa     420
gccacggcta actacgtgcc agcagccgcg gtaatacgta ggtggcaagc gttatccgga     480
attattgggc gtaaagcgcg cgtaggcggt ttttttaagtc tgatgtgaaa gcccacggct     540
caaccgtgga gggtcattgg aaactggaaa acttgagtgc agaagaggaa agtggaattc     600
catgtgtagc ggtgaaatgc gcagagatat ggaggaacac cagtggcgaa ggcgactttc     660
tggtctgtaa ctgacgctga tgtgcgaaag cgtggggatc aaacaggatt agatacctg      720 gtagtccacg ccgtaaacga tgagtgctaa gtgttagggg gtttccgccc cttagtgctg     780
cagctaacgc attaagcact ccgcctgggg agtacgaccg caaggttgaa actcaaagga     840
attgacgggg acccgcacaa gcggtggagc atgtggttta attcgaagca acgcgaagaa     900
ccttaccaaa tcttgacatc ctctgacccc tctagagata gagttttccc cttcggggga     960
```

| | | | |
|---|---|---|---|
| cagagtgaca | ggtggtgcat | ggttgtcgtc agctcgtgtc | gtgagatgtt gggttaagtc | 1020 |
| ccgcaacgag | cgcaacccctt | aagcttagtt gccatcatta | agttgggcac tctaagttga | 1080 |
| ctgccggtga | caaaccggaa | gaaaggtggg g | | 1111 |

<210> SEQ ID NO 2
<211> LENGTH: 1000
<212> TYPE: DNA
<213> ORGANISM: Acinetobacter lwoffii

<400> SEQUENCE: 2

| | | | | |
|---|---|---|---|---|
| tgggtaaag | gcctaccaag | gcgacgatct | gtagcgggtc tgagaggatg | atccgccaca | 60 |
| ctgggactga | gacacggccc | agactcctac | gggaggcagc agtggggaat | attggacaat | 120 |
| gggggggaacc | ctgatccagc | catgccgcgt | gtgtgaagaa ggccttttgg | ttgtaaagca | 180 |
| cttttaagcga | ggaggaggct | accgagatta | atactcttgg atagtggacg | ttactcgcag | 240 |
| aataagcacc | ggctaactct | gtgccagcag | ccgcggtaat acagagggtg | caagcgttaa | 300 |
| tcggatttac | tgggcgtaaa | gcgcgcgtag | gtggccaatt aagtcaaatg | tgaaatcccc | 360 |
| gagcttaact | tgggaattgc | attcgatact | ggttggctag agtatgggag | aggatggtag | 420 |
| aattccaggt | gtagcggtga | aatgcgtaga | gatctgagg aataccgatg | gcgaaggcag | 480 |
| ccatctggcc | taatactgac | actgaggtgc | gaaagcatgg ggagcaaaca | ggattagata | 540 |
| ccctggtagt | ccatgccgta | aacgatgtct | actagccgtt ggggcctttg | aggctttagt | 600 |
| ggcgcagcta | acgcgataag | tagaccgcct | ggggagtacg gtcgcaagac | taaaactcaa | 660 |
| atgaattgac | gggggcccgc | acaagcggtg | gagcatgtgg tttaattcga | tgcaacgcga | 720 |
| agaaccttac | ctggtcttga | catagtaaga | actttccaga gatggattgg | tgccttcggg | 780 |
| aacttacata | caggtgctgc | atggctgtcg | tcagctcgtg tcgtgagatg | ttgggttaag | 840 |
| tcccgcaacg | agcgcaaccc | ttttccttat | tgccagcgg gttaagccgg | aactttaag | 900 |
| gatactgcca | gtgacaaact | ggaggaaggc | ggggacgacg tcaagtcatc | atggccctta | 960 |
| cgaccagggc | tacacacgtg | ctacaatggt | cggtacaaag | | 1000 |

<210> SEQ ID NO 3
<211> LENGTH: 848
<212> TYPE: DNA
<213> ORGANISM: Propionibacterium acnes

<400> SEQUENCE: 3

| | | | | |
|---|---|---|---|---|
| ggtagccggc | ctgagagggt | gaccggccac | attgggactg agatacggcc | cagactccta | 60 |
| cgggaggcag | cagtggggaa | tattgcacaa | tgggcggaag cctgatgcag | caacgccgcg | 120 |
| tgcgggatga | cggccttcgg | gttgtaaacc | gctttcgcct gtgaccaagc | gtgagtgacg | 180 |
| gtaatgggta | agaagcacc | ggctaactac | gtgccagcag ccgcggtgat | acgcagggtg | 240 |
| cgagcgttgt | ccggatttat | tgggcgtaaa | gggctcgtag gtggttgatc | gcgtcggaag | 300 |
| tgtaatcttg | gggcttaacc | ctgagcgtgc | tttcgatacg ggttgacttg | aggaaggtag | 360 |
| gggagaatgg | aattcctggt | ggagcggtgg | aatgcgcaga tatcaggagg | aacaccagtg | 420 |
| gcgaaggcgg | ttctctgggc | cttttcctgac | gctgaggagc gaaagcgtgg | ggagcgaaca | 480 |
| ggcttagata | ccctggtagt | ccacgctgta | aacggtgggt actaggcgtg | ggtccattc | 540 |
| caccgggttc | cgtggccgta | gctaacgctt | caagtacccc gcctggggag | tacggccgca | 600 |
| aggctaaaac | tcaaaggaat | tgacgggcc | ccgcacaagc ggcggagcat | gcggattaat | 660 |
| tagatgccac | gcctagaacc | ttacctgggc | ttgacacgga tcgggagtgc | tcagagatgg | 720 |

```
gtgtgcgctc ttttggggtc ggttcacagg cggtgcatgg ctgtcgtcag ctcgtgtcgt    780
gagatgttgg gataagtccc gcaacgagcg caacccttct tccctgctgc cagcacgtta    840
tggcgggg                                                             848
```

<210> SEQ ID NO 4
<211> LENGTH: 795
<212> TYPE: DNA
<213> ORGANISM: Enhydrobacter aerosaccus

<400> SEQUENCE: 4

```
ccggactcct acgggaggca gcagtgggga atattggaca atgggggcaa ccctgatcca     60
gccatgccgc gtgtgtgaag aaggcctttt ggttgtaaag cactttaagc agggaggaga    120
ggctaatggt taatacccat tagattagac gttacctgca gaataagcac cggctaactc    180
tgtgccagca gccgcggtaa tacagagggt gcgagcgtta atcggaatta ctgggcgtaa    240
agcgagtgta ggtggctcat taagtcacat gtgaaatccc cggcttaac ctgggaactg     300 catgtgatac tggtggtgct agaatatgtg agagggaagt agaattccag gtgtagcggt    360
gaaatgcgta gagatctgga ggaataccga tggcgaaggc agcttcctgg cataatattg    420
acactgagat cgaaagcgt gggtagcaaa caggattaga taccctggta gtccacgccg      480
taaacgatgt ctactagccg ttggggtcct tgagacttta gtggcgcagt taacgcgata    540
agtagaccgc ctgggagta cggccgcaag gttaaaactc aaatgaattg acggggcc        600 gcacaagcgg tggagcatgt ggtttaattc gatgcaacgc gaagaacctt acctggtgct    660
atgactcata gctgagaatg ctgctgcaga gatgagagag tgccttcggg aactcacata    720
caggtgctgc atggctgtcg tcagctcgtg tcgtgagatg ttgggttaag tcccgcaacg    780
agcgcaaccc ttttc                                                    795
```

<210> SEQ ID NO 5
<211> LENGTH: 642
<212> TYPE: DNA
<213> ORGANISM: Corynebacterium tuberculostearicum

<400> SEQUENCE: 5

```
cgggtgagta acacgtgggt gatctgccct gcacttcggg ataagcctgg gaaactgggt     60
ctaataccgg ataggagcca ttttttagtgt gatggttgga aagttttttc ggtgtaggat   120
gagctcgcgg cctatcagct tgttggtggg gtaatggcct accaaggcgg cgacgggtag    180
ccggcctgag agggtggacg gccacattgg gactgagata cggcccagac tcctacggga    240
ggcagcagtg gggaatattg cacaatgggc gcaagcctga tgcagcgacg ccgcgtgggg    300
gatgacggcc ttcgggttgt aaactccttt cgctagggac gaagcttttt gtgacggtac    360
ctagataaaa agcaccggct aactacgtgc cagcagccgc ggtaatacgt agggtgcgag    420
cgttgtccgg aattactggg cgtaaagggc tcgtaggtgg tttgtcgcgt cgtctgtgaa    480
attccggggc ttaactccgg gcgtgcaggc gatacggcca acttgagt actgtagggg      540 taactggaat tcctggggta gcgctgaaat gcgcagatat caggaggaac accgatggcg    600
aaggcaggtt actgggcagt tactgacgct gagaagcgaa ag                       642
```

<210> SEQ ID NO 6
<211> LENGTH: 1054
<212> TYPE: DNA
<213> ORGANISM: Corynebacterium amycolatum

<400> SEQUENCE: 6

```
gtggcgaacg ggtgagtaac acgtgggtga cctgccctgc acttcgggat aagcctggga    60
aactgggtct aataccggat aggaccgcac cgtgagggtg tggtggaaag ttttttcggt   120
gtgggatggg cccgcggcct atcagcttgt tggtggggta atggcctacc aaggcggcga   180
cgggtagccg gcctgagagg gtggacggcc acattgggac tgagacacgg cccagactcc   240
tacgggaggc agcagtgggg aatattgcac aatgggcgga agcctgatgc agcgacgccg   300
cgtgggggat gacggccttc gggttgtaaa ctcctttcac catcgacgaa gggtttctga   360
cggtagatgg agaagaagca ccggctaact acgtgccagc agccgcggta atacgtaggg   420
tgcgagcgtt gtccggaatt actgggcgta aagagctcgt aggtggtttg tcgcgtcgtc   480
tgtgaaattc cggggcttaa ctccgggcgt gcaggcgata cgggcataac ttgagtactg   540
taggggagac tggaattcct ggtgtagcgg tgaaatgcgc agatatcagg aggaacaccg   600
gtggcgaagg cgggtctctg gcagtaact gacgctgagg agcgaaagca tgggagcga    660
acaggattag ataccctggt agtccatgcc gtaaacggtg ggcgctaggt gtgggtttcc   720
ttccacggga tccgtgccgt agctaacgca ttaagcgccc cgcctgggga gtacggccgc   780
aaggctaaaa ctcaaaggaa ttgacggggg cccgcacaag cggcggagca tgtggattaa   840
ttcgatgcaa cgcgaagaac cttacctggg cttgacatat acaggatcgc gccagagatg   900
gtgtttccct tgtggcttgt atacaggtgg tgcatggttg tcgtcagctc gtgtcgtgag   960
atgttgggtt aagtcccgca acgagcgcaa cccttgtctt atgttgccag cacgttgtgg  1020
tgggggactc gtaaagaaac tgcccggggt taac                              1054
```

<210> SEQ ID NO 7
<211> LENGTH: 1082
<212> TYPE: DNA
<213> ORGANISM: Staphylococcus hominis

<400> SEQUENCE: 7

```
gttagcggcg gacgggtgag taacacgtag gtaacctacc tataagactg ggataacttc    60
gggaaaccgg agctaatacc ggataatatt tcgaaccgca tggttcgata gtgaaagatg   120
gctttgctat cacttataga tggacctgcg ccgtattagc tagttggtaa ggtaacggct   180
taccaaggca acgatacgta gccgacctga gagggtgatc ggccacactg gaactgagac   240
acggtccaga ctcctacggg aggcagcagt agggaatctt ccgcaatggg cgaaagcctg   300
acggagcaac gccgcgtgag tgatgaaggt cttcggatcg taaaactctg ttattaggga   360
agaacaaacg tgtaagtaac tgtgcacgtc ttgacggtac ctaatcagaa agccacggct   420
aactacgtgc cagcagccgc ggtaatacgt aggtggcaag cgttatccgg aattattggg   480
cgtaaagcgc gcgtaggcgg ttttttaagt ctgatgtgaa agcccacggc tcaaccgtgg   540
agggtcattg gaaactggaa aacttgagtg cagaagagga agtggaatt cctggtgtag   600
cggtgaaatg cgcagagata tggaggaaca ccagtggcga aggcgacttt ctggtctgta   660
actgacgctg atgtgcgaaa gcgtggggat caaacaggat tagataccct ggtagtccac   720
gccgtaaacg atgagtgcta agtgttaagg gggtttccgc cccttagtgc tgcagctaac   780
gcattaagca ctccgcctgg ggagtacgac cgcaaggttg aaactcaaag gaattgacgg   840
ggacccgcac aagcggtgga gcatgtggtt taattcgaag caacgcgaag aaccttacca   900
aatcttgaca tccttcgacc cttctagaag atagaagttt cccctccggg ggacaaagtg   960
acaggtggtg catggttgtc gtcagctcgt gtcgtgagat gtttgggtta agtcccgcaa  1020
```

```
cgagcgcaac ccttaagctt agttgccatc attaagttgg gcactctaag ttgactgccg    1080
gt                                                                   1082

<210> SEQ ID NO 8
<211> LENGTH: 579
<212> TYPE: DNA
<213> ORGANISM: Enterobacter cloacae

<400> SEQUENCE: 8
gagtggcgga cgggtgagta atgtctggga aactgcctga tggagggggga taactactgg    60 aaacggtagc taataccgca taatgtcgca agaccaaaga gggggacctt cgggcctctt   120
gccatcagat gtgcccagat gggattagct agtaggtggg gtaacggctc acctaggcga   180
cgatccctag ctggtctgag aggatgacca gccacactgg aactgagaca cggtccagac   240
tcctacggga ggcagcagtg gggaatattg cacaatgggc gcaagcctga tgcagccatg   300
ccgcgtgtat gaagaaggcc ttcgggttgt aaagtacttt cagcggggag gaaggtgttg   360
tggttaataa ccgcagcaat tgacgttacc cgcagaagaa gcaccggcta actccgtgcc   420
agcagccgcg gtaatacgga gggtgcaagc gttaatcgga attactgggc gtaaagcgca   480
cgcaggcggt ctgtcaagtc ggatgtgaaa tccccgggct caacctggga actgcattcg   540
aaactggcag gctggagtct tgtagagggg ggtagaatt                           579

<210> SEQ ID NO 9
<211> LENGTH: 887
<212> TYPE: DNA
<213> ORGANISM: Micrococcus luteus

<400> SEQUENCE: 9
gggtgagtaa cacgtgagta acctgcccctt aactctggga taagcctggg aaactgggtc    60
taataccgga taggagcgcc caccgcatgg tgggtgttgg aaagatttat cggttttgga   120
tggactcgcg gcctatcagc ttgttggtga ggtaatggct caccaaggcg acgacgggta   180
gccggcctga gagggtgacc ggccacactg ggactgagac acggcccaga ctcctacggg   240
aggcagcagt ggggaatatt gcacaatggg cgaaagcctg atgcagcgac gccgcgtgag   300
ggatgacggc cttcgggttg taaacctctt tcagtaggga agaagcgaaa gtgacggtac   360
ctgcagaaga agcaccggct aactacgtgc cagcagccgc ggtaatacgt agggtgcgag   420
cgttatccgg aattattggg cgtaaagagc tcgtaggcgg tttgtcgcgt ctgtcgtgaa   480
agtccggggc ttaaccccgg atctgcggtg ggtacgggca gactagagtg cagtagggga   540
gactggaatt cctggtgtag cggtggaatg cgcagatatc aggaggaaca ccgatggcga   600
aggcaggtct ctgggctgta actgacgctg aggagcgaaa gcatgggag cgaacaggat   660 tagataccct ggtagtccat gccgtaaacg ttgggcacta ggtgtgggga ccattccacg   720
gtttccgcgc cgcagctaac gcattaagtg ccccgcctgg ggagtacggc cgcaaggcta   780
aaactcaaag gaattgacgg gggcccgcac aagcggcgga gcatgcggat taattcgatg   840
caacgcgaaa gaaccttacc aaggcttgac atgttctcga tcgccgt                 887
```

PREBIOTIC SKIN CARE COMPOSITIONS CONTAINING CARBOXYLIC ACIDS

CROSS-REFERENCE TO RELATED APPLICATIONS

This application is a national phase entry under 35 U.S.C. § 371 of International Patent Application PCT/EP2020/061119, filed Apr. 22, 2020, designating the United States of America and published as International Patent Publication WO 2020/216757 A1 on Oct. 29, 2020, which claims the benefit under Article 8 of the Patent Cooperation Treaty to European Patent Application Serial No. 19171010.2, filed Apr. 25, 2019.

TECHNICAL FIELD

The disclosure relates to the field of reducing malodor due to bacterial conversion of molecules that are present in sweat. Indeed, the disclosure describes the usage of specific that which steer the microbiome by inhibiting the growth of specific odor-producing bacteria and/or promoting the growth of bacteria known to be beneficial in relation to malodor. The acids of the disclosure can be used in deodorants, washing powders, clothing finishing agents or any method to reduce malodor. The disclosure thus relates to the usage of a topical composition as a prebiotic.

STATEMENT ACCORDING TO 37 C.F.R. § 1.821(c) or (e)—SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

Sterile sweat is odorless. The bacteria living in the underarm convert sweat molecules and depending on the kind of bacteria, that odor can be bad. The mode of action of current deodorants relies on the addition of perfume, to mask the malodor production, and the addition of antimicrobial compounds. Compounds that possess an antimicrobial and antifungal function and thus are commonly used in deodorants are triclosan, triclocarsan, quaternary ammonium compounds, metal salts, aliphatic alcohols and glycols and other fragrances (1)(2). Antiperspirants, on the other hand, are a subgroup of deodorants that act similarly but additionally, they prevent sweating by blocking the sweat glands. Antiperspirants have a third mode of action caused by aluminum salts, which is known to block the sweat glands by mechanical obstruction. The ingredients normally used in antiperspirants are aluminum chloride hexahydrate (ACH) (in low concentrations), aluminum chlorohydrate, aluminum sesquichlorohydrate, aluminum chlorohydrex and aluminum zirconium tetrachlorohydrate.

By using underarm antiperspirants and deodorants, a microbial shock is caused to the underarm microbiome, which leads to an increase of the microbial diversity. A higher microbial diversity is associated with more underarm malodor. For certain individuals, the relative abundance of corynebacteria increased, which suggests that using an antiperspirant could lead toward a more malodorous microbiome (3)(4).

It is impossible to remove all odor-producing bacteria by washing the underarm. Bacteria will always remain in the hair follicles and sweat glands. Deodorants of today are not designed to "help" the underarm microbiome.

Axillary malodor is generated due to bacterial biotransformation of underarm secretions. Typical human, unusual, methyl-branched, odd-numbered long-chain fatty acids (LCFA) are degraded via β-oxidation into short-chain, volatile fatty acids (VFAs) (5)(6). Additionally, the release of short-chain fatty acids, such as E-3-methyl-2-hexenoic acid (3M2H), 3-hydroxy-3-methyl-hexanoic acid (HMHA), 3-hydroxy-3-methylhexanoic acid (3M3H), and a wide range of other structurally unusual VFAs, secreted as L-glutamine conjugates in apocrine glands, are considered as major components of the axillary malodor (7)(8)(9). After secretion by apocrine sweat glands, bacteria remove the L-glutamine residue with Na-acyl-glutamine aminoacylase and consequently releasing the VFAs. Several thioalcohols, such as 3-methyl-3-sulfanyl-hexan-1-ol (3M3SH) and 2-methyl-3-sulphanylbutan-1-ol (2M3SB), as well as their isomers were also reported as important contributors to axillary malodor (10)(11)(12). Thioalcohols can produce a sulphuric, meaty, onion-like or even fruity smell (6). Thioalcohols are secreted by apocrine sweat glands as cysteine- or cysteine-glycine conjugates (9). Steroids secreted in the underarm through the apocrine glands secrete a series of steroids, through the ABCC11 gene (13). The bacterial breakdown products, although not fully characterized, are known to cause a specific malodor (14).

At present, there is still a need to find alternative methods to combat odor-producing bacteria.

Methods upon today merely focus on inhibition of the malodor associated bacteria. For instance, U.S. Pat. No. 6,171,582 uses agents that inactivate the malodor associated corynebacteria. Those agents include salicylic acid, benzoic acid, ferulic acid, amongst others (15). EP 1902754 describes a deodorant composition using a salt of zinc and salicylic acid, amongst others, that have a bactericidal effect, and thus inhibit the bacteria to obtain a deodorant activity. GB 2284762 describes the use of talc, starch, boric acid and salicylic acid to prevent the formation of microbes on feet that lead to bad odors. U.S. Pat. No. 7,569,530 discloses pyroglutamic acid, adipic acid, gluconic acid, gluconolactone acid, glutamic acid, glutaric acid, glycolic acid, tartaric acid, ascorbic acid, benzoic acid, salicylic acid, citric acid, malic acid, succinic acid, lactic acid as an antimicrobial composition. WO2019011551 discloses anions of, for instance, lactates, citrates, and tartrates, to reduce the coryneform bacteria. JPH0622540 discloses malic acid, citric acid, tartaric acid and gluconic acid, amongst others, that have an antibacterial effect. The latter documents thus describe the inhibition or inactivation of bacteria to obtain a deodorant activity. Also the existing products on the market mainly focus on antibacterial ingredients to combat malodor.

JP2005270453 describes the use of gallic acid, tannic acid and caffeic acid to deodorize odors of sulfur and nitrogen compounds.

WO 2020/052916 describes a saccharide isomerate for use as prebiotic ingredient for skin microbiome balancing. US20150202136 describes a list of ingredients claimed to increase the number of anaerobic and/or aerobic skin commensal microorganisms on skin. JP2017008095 discloses a galactooligosaccharide for promotion of growth of *Staphylococcus epidermidis*, *Corynebacterium jeikeium*, and *Propionibacterium acnes*. DE102005012476 discloses ingredients, such as carboxylic acids, dicarboxylic acid, metal salts, amongst others, that specifically target *Staphylococcus*

*hominis* sp. US 20160089395 describes arginine bicarbonate and zinc carbonate to inhibit the growth of pathogenic *Staphylococcus aureus* and promote the growth of non-pathogenic *Staphylococcus epidermidis*.

There is still a need to provide compounds that are capable to selectively stimulate good-odor associated bacteria and/or to selectively inhibit malodorous bacteria.

BRIEF SUMMARY

The disclosure describes 25 acids that can specifically enrich the good odor associated bacteria and/or specifically inhibit the malodor associated bacteria, both with the aim of reducing malodor in skin or textiles.

In other words, the disclosure describes 25 acids, which steer the microbiome to a better smelling microbiome in a very specific manner as the latter acids specifically promote the growth of good-odor associated bacteria such as *Staphylococcus epidermidis, Acinetobacter lwoffii, Propionibacterium acnes* (*Cutibacterium acnes*) and *Enhydrobacter aerosaccus* bacteria and do not promote and/or inhibit the growth of mal-odor associate bacteria such as *Corynebacterium tuberculostearicum, Corynebacterium amycolatum, Staphylococcus hominis, Micrococcus luteus* and *Enterobacter cloacae*.

Hence, the disclosure relates in first instance to the usage of a composition to selectively promote the growth, metabolism and/or colonization of good-odor associated bacteria and/or to selectively inhibit the growth, metabolism and/or colonization of malodor-associated bacteria, wherein the composition comprises at least one acid chosen from the list consisting of: gallic acid, fumaric acid, mucic acid, γ-aminobutyric acid, α-keto-glutaric acid, quinic acid, D-saccharic acid, glyoxylic acid, D-glucosaminic acid, 4-hydroxybenzoic acid, D,L-α-amino-caprylic acid, N-acetyl-neuraminic acid, D,L-α-amino-N-butyric acid, orotic acid, ε-amino-N-caproic acid, β-hydroxybutyric acid, tropic acid and hippuric acid.

The disclosure further relates to the usage of a composition to selectively promote the growth, metabolism and/or colonization of good-odor associated bacteria, wherein the composition comprises at least one acid chosen from the list consisting of: tricarballylic acid, L-lactic acid, citric acid, D,L-malic acid, stearic acid, acetic acid and ferulic acid.

More specifically, the disclosure relates to the usage as described above wherein the good-odor associated bacteria are at least *Staphylococcus epidermidis, Acinetobacter* spp, *Propionibacterium acnes* (*Cutibacterium acnes*) or *Enhydrobacter aerosaccus* bacteria and wherein the malodor-associated bacteria are at least *Corynebacterium tuberculostearicum, Corynebacterium amycolatum, Staphylococcus hominis, Micrococcus luteus* or *Enterobacter cloacae*.

Furthermore, the disclosure relates to the usage of a composition as described above, wherein the composition is provided as a topical formulation selected from the group selected from soap, spray, drop, aerosol, powder, roll-on, lotion, cream, stick, solution, sachet, colloidal suspension, film, patch, finishing agent and ointment.

The disclosure further relates to the usage of a composition as described above, wherein the composition has—upon application—a pH between 3.5 and 7.

The disclosure further relates to the usage of a composition as described above to modify the underarm microbiome, skin microbiome, clothing microbiome or any other fabric microbiome.

The disclosure further relates to the usage of a composition as described above to reduce the formation of short-chain fatty acids released from unusual, methyl-branched, odd-numbered long-chain fatty acids; reduce the formation of E-3-methyl-2-hexenoic acid, 3-hydroxy-3-methylhexanoic acid and 3-hydroxy-3-methylhexanoic acid; and, reduce the formation of thioalcohols such as 3-methyl-3-sulfanyl-hexan-1-ol and 2-methyl-3-sulphanylbutan-1-ol.

The disclosure further relates to the usage of composition as described above as a prebiotic ingredient.

BRIEF DESCRIPTION OF THE DRAWINGS

FIG. 1. Growth/inhibition of good-odor associated bacteria relative to malodor associated bacteria of phenotype microarray plate with an assortment of acids. Compounds on the left of the x-axis stimulate the growth of all good-odorous bacteria in this experiment combined, while compounds on the right stimulate the growth of malodorous bacteria in the experiment combined. Compounds such as gallic acid, tricarballylic acid, and lactic acid stimulate the growth of good-odorous bacteria minimum 0.5 times better than the growth of malodorous bacteria.

DETAILED DESCRIPTION

The disclosure relates to the following compounds/acids that selectively steer the microbiome toward a better smelling microbiome: gallic acid, tricarballylic acid, L-lactic acid, fumaric acid, mucic acid, citric acid, D,L-malic acid, stearic acid, γ-aminobutyric acid, α-keto-glutaric acid, acetic acid, quinic acid, D-saccharic acid, glyoxylic acid, D-glucosaminic acid, 4-hydroxybenzoic acid, D,L-α-amino-caprylic acid, N-acetyl-neuraminic acid, D,L-α-amino-N-butyric acid, orotic acid, ferulic acid, ε-amino-N-caproic acid, β-hydroxybutyric acid, tropic acid, and hippuric acid.

The disclosure thus relates in first instance to the usage of specific acids, which promote the growth of good-odor-associated bacteria such as *Staphylococcus epidermidis, Acinetobacter* spp, *Propionibacterium acnes* (*Cutibacterium acnes*) and *Enhydrobacter aerosaccus* bacteria and do not promote (or inhibit) the growth of malodor-associated bacteria such as *Corynebacterium tuberculostearicum, Corynebacterium amycolatum, Staphylococcus hominis, Micrococcus luteus* and *Enterobacter cloacae* bacteria, wherein the composition comprises at least one acid chosen from the list consisting of: gallic acid, tricarballylic acid, L-lactic acid, fumaric acid, mucic acid, citric acid, D,L-malic acid, stearic acid, γ-aminobutyric acid, α-keto-glutaric acid, acetic acid, quinic acid, D-saccharic acid, glyoxylic acid, D-glucosaminic acid, 4-hydroxybenzoic acid, D,L-α-amino-caprylic acid, N-acetyl-neuraminic acid, D,L-α-amino-N-butyric acid, orotic acid, ferulic acid, ε-amino-N-caproic acid, β-hydroxybutyric acid, tropic acid, and hippuric acid.

All of the above-listed compounds/acids are well-known and can be easily obtained through normal commercial canals. Compounds are relatively cheap, easily accessible, odorless or have a pleasant odor (or no malodor at the least), light or no color and non-toxic to mammals/humans in the concentrations used in the experiments.

The following table shows the structure of each of the above-indicated acids:

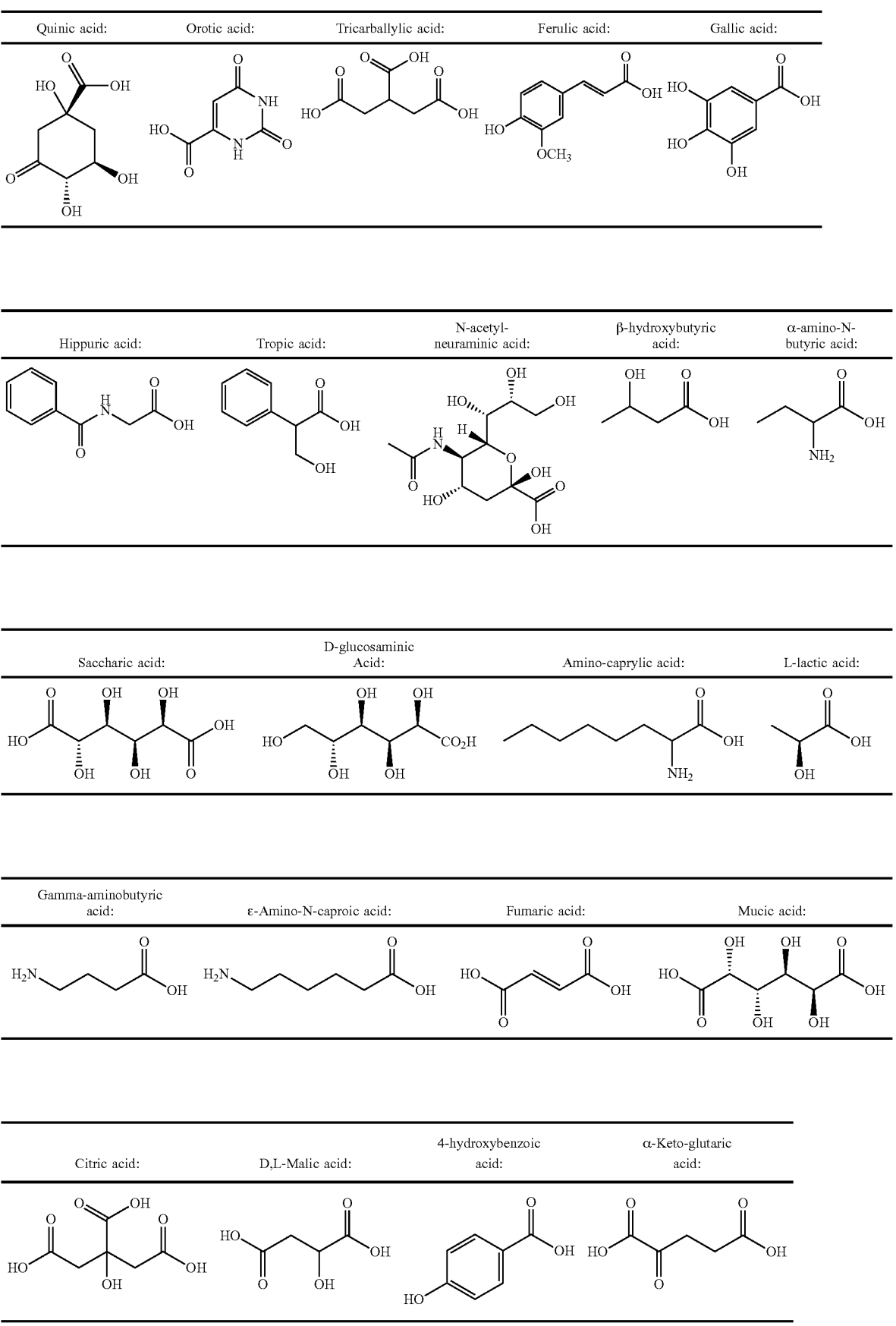

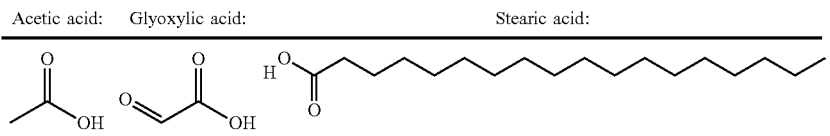

Bacterial growth is measured with Optical Density (OD) measurements at wavelength 620 nm with every sample analyzed in triplicate. Promoting bacterial growth relates to a higher bacterial biomass density in suspension after 24 h, as measured with the spectrophotometer. Bacterial inhibition relates to a similar or lower bacterial density after 24 h in suspension, as measured with the spectrophotometer. Promoting bacterial metabolism relates to a higher bacterial activity, and thus active gene expression of the bacteria of interest. Inhibiting bacterial metabolism relates to a lower bacterial activity, and thus less gene expression of the bacteria of interest. Bacterial metabolism can be measured by metatranscriptomics analysis, RNA-sequencing or any ELISA kit measuring specific enzymes of the metabolism.

Furthermore, the disclosure relates to the usage of the acids as indicated above in a deodorant or skin cosmetics. A deodorant is any product applied in the underarm region to mask or reduce underarm odor. Deodorant compositions as described herein are administered, preferably topically, for the treatment of any one or more symptoms desirable of change, e.g., cutaneous (including axillary) malodor. A skin cosmetic is any product applied to the skin to improve its appearance. Dosage forms are solid or free-flowing. Dosage forms include, but are not limited to, soaps, sprays, drops, aerosols, powders, roll-ons, lotions, creams, sticks, solutions, sachets, colloidal suspensions, films, patches and ointments. Deodorants or skin cosmetics can be applied on skin, for example, the underarm or foot or other body parts, or, on clothes.

Furthermore, the disclosure relates to a fabric care product, textile finishing product, coating or washing powder. The compounds listed in this invention is applied or coated on clothing textiles, sport textiles, bed linen, intimate clothing, feet clothing (socks and shoes), carpets, or other textiles to reduce the malodor formation. The compounds listed in this invention is applied in the laundry machine or elsewhere in the household to reduce malodor formation. The compounds listed in this invention is used as washing powder to rinse the textiles. Dosage forms are solid or free-flowing. Dosage forms include, but are not limited to, powders, soaps, sprays, drops, aerosols, powders, roll-ons, lotions, creams, sticks, solutions, sachets, colloidal suspensions, films, patches and ointments. Hence, the disclosure relates to the usage of a composition as described above, wherein the composition is provided as a topical formulation selected from the group selected from soap, spray, drop, aerosol, powder, roll-on, lotion, cream, stick, solution, sachet, colloidal suspension, film, patch, finishing agent and ointment. The invention further relates to the usage of a composition as described above to modify the underarm microbiome, skin microbiome, clothing microbiome or any other fabric microbiome.

Deodorant or clothing product/composition as described herein may have a pH of at least 3.0, 4.0. 5.0, 6.0, 7.0, 8.0, 9.0, or 10.0 upon administration and/but have preferably a pH between 3.5 and 7.

The disclosure further relates to the usage of a composition/acids as described above to modify the microbiome.

Staphylococcus epidermidis is a major member of the skin microbiome, which is correlated to a better underarm/skin odor and a lower bacterial diversity. Other bacteria such as, and not limited to, Acinetobacter spp, Propionibacterium acnes (Cutibacterium acnes) and Enhydrobacter aerosaccus, are associated with a good skin odor. These bacteria are here called "good odor associated bacteria." Corynebacterium spp. (containing and not limited to C. tuberculostearicum, C. amycolatum) are correlated with more skin malodor and/or a higher bacterial diversity. Other bacteria, such as, and not limited to, Staphylococcus hominis, Micrococcus luteus and Enterobacter cloacae, are associated to malodor and/or a higher bacterial diversity. These bacteria are here referred to as "malodor associated bacteria." All of the isolates combined represent about 81% of the average in vivo underarm microbiome (16), which gives a good representation of the underarm microbiome. Modifying the microbiome relates to steering the microbiome to a higher abundance of good-odor associated bacteria and a lower abundance of malodor associated bacteria. The microbiome can be modified in the underarm region, on skin, on clothes, on other skin regions of the human body or in washing machines. Good odor associated bacteria are associated with a positive hedonic value, which relates to the pleasantness of the odor—on a scale from −8 (very unpleasant) to 0 (neutral) to +8 (very pleasant). Good odor associated bacteria are also involved in a lower intensity of the odor, which relates to the quantity of the odor—on a scale from 0 (no odor) to +10 (very strong/intolerable). Malodor associated bacteria are associated with a low hedonic value and a high odor intensity.

Hence, the disclosure specifically relates to the usage of a composition as defined above wherein the microbiome comprises bacteria of at least one of the following the species: Staphylococcus epidermidis, Acinetobacter lwoffii, Propionibacterium acnes (Cutibacterium acnes), Staphylococcus hominis, Corynebacterium tuberculostearicum, Corynebacterium amycolatum, Micrococcus luteus, Enhydrobacter aerosaccus, Enterobacter cloacae.

The disclosure relates—in other words—to a method to reduce malodor comprising administering an effective amount of a composition as defined above to a mammal in need thereof. An effective amount is amount of compound that can have an impact on the microbiome.

Skin and textile malodor is generated due to bacterial biotransformation of sweat secretions. Typical human, unusual, methyl-branched, odd-numbered long-chain fatty acids (LCFA) are degraded via β-oxidation into short-chain, volatile fatty acids (5,6). Additionally, the release of short-chain fatty acids, such as E-3-methyl-2-hexenoic acid (3M2H), 3-hydroxy-3-methyl-hexanoic acid (HMHA), 3-hydroxy-3-methylhexanoic acid (3M3H), and a wide range of other structurally unusual VFAs, secreted as L-glutamine conjugates in apocrine glands, are considered as major components of the axillary malodor (7-9). After secretion by apocrine sweat glands, bacteria remove the L-glutamine residue with $N^{\alpha}$-acyl-glutamine aminoacylase and consequently releasing the VFAs. Several thioalcohols, such as 3-methyl-3-sulfanyl-hexan-1-ol (3M3SH) and 2-methyl-3-sulphanylbutan-1-ol (2M3SB), as well as their isomers were also reported as important contributors to axillary malodor (10-12).

Therefore, the disclosure further relates to a method—or the usage of a composition as described above- to reduce the formation of short-chain fatty acids released from unusual, methyl-branched, odd-numbered long-chain fatty acids; reduce the formation of E-3-methyl-2-hexenoic acid, 3-hydroxy-3-methyl-hexanoic acid and 3-hydroxy-3-methyl-hexanoic acid; and, reduce the formation of thioalcohols such as 3-methyl-3-sulfanyl-hexan-1-ol and 2-methyl-3-sulphanylbutan-1-ol comprising administering an effective amount of a composition as defined above to a mammal in need thereof.

The disclosure relates to prebiotic ingredients to steer the microbiome toward a less odorous microbiome.

The disclosure also relates to a method as defined above wherein the malodor is situated on the skin or hair of the mammal.

The disclosure also relates to a method as defined above wherein the malodor is situated in the underarm of the mammal.

The disclosure also relates a to a method as defined above wherein the malodor is situated in the household, clothing textiles, washing machine, fabrics or shoes of the mammal.

The disclosure further relates to a method as defined above wherein the mammal is a human.

The disclosure further relates to the usage of composition as described above as a prebiotic ingredient. With the term "prebiotic ingredient" is meant that the carboxylic acid stimulates the growth, metabolic activity and/or colonization of the beneficial bacteria. As such, the disclosure steers the microbiome toward a less odorous and better microbiome.

The disclosure will now be illustrated with the following, non-limiting examples.

Examples

Materials and Methods 1.1 Growth Media & Solutions
1.1.1 Axillary Growth Medium

To grow the axillary bacteria on an agar plate, axillary culture blood agar (ACX) was used. To compose 500 mL of this medium, one needs:
  19.75 g blood agar base no. 2 (Oxoid LTD, Basingstoke, England)
  1.5 g yeast extract (Oxoid LTD, Basingstoke, England)
  1 g glucose (Carlroth GmbH, Karlsruhe, Germany)
  2.5 mL TWEEN® 80 (Sigma Aldrich, St. Louis, USA)
  25 mL defibrinated horse blood (Oxoid Limited, Basingstoke, England)

When the first four components were added to a Schott bottle of 500 mL, the solution is diluted with distilled water until a volume of ca. 475 mL is reached. After autoclaving and cooling down at about 40° C., the defibrinated horse blood is added. Immediately after the blood is added, the medium is poured in plates in a sterile way and one have to wait until it is fixed. The plates were stored in the cold room (ca. 4° C.).

1.1.2 Nutrient Broth

Axillary bacteria were cultured in liquid medium using nutrient broth. To compose 500 mL nutrient broth, 6.5 g nutrient broth without agar (Oxoid LTD, Basingstoke, Hampshire, England) was added to a Schott bottle of 500 mL. The bottle was diluted with distilled water until 500 mL. Afterwards, the bottle was shaken and autoclaved. Finally, the bottle was distributed over 10 mL tubes in a sterile manner. The tubes were stored in a cold room (ca. 4° C.) to make sure they remain sterile.

1.1.3 M9 Medium

M9 medium is a minimal-growth-medium for bacteria. Bacteria were diluted and distributed in 96-well plates using M9 medium, containing the minimal salts and micro-nutrients. This medium provides enough nutrients for the bacteria to survive, but not to grow. To create 1 L of this medium, one needs at first a salt solution (1 L) that consists of:
  42 g $Na_2HPO_4 \cdot 7H_2O$
  15 g $KH_2PO_4$
  2.5 g NaCl
  5 g $NH_4Cl$ All compounds (originating from Carl Roth GmbH, Karlsruhe, Germany) were added to a Schott bottle of 1 L, which is diluted with distilled water until one reaches 1 L. Next, this solution was autoclaved. In addition to the salt solution, two separate solutions with 120 g/L $MgSO_4$ and 110 g/L $CaCl_2$) were prepared. The chemical compounds originated again from Carl Roth GmbH, Karlsruhe, Germany. These solutions were sterilized using a filter with a pore size of 0.22 μm (Sartorius Stedim Biotech S.A., Brussels, Belgium). For 1 L M9 medium, 200 mL salt solution was combined with 2 mL $MgSO_4$ solution and 0.1 mL $CaCl_2$) solution. This solution was diluted with autoclaved distilled water until 1 L is reached (17).

1.1.4 PBS-Solution

To dilute the samples and make them suitable for measurements using the flow cytometry, a phosphate-buffered saline solution (PBS) was needed. One needed to put one tablet of 2 g in 200 mL of distilled water in order to receive a 0.01M phosphate buffer, 0.0027M potassium chloride and 0.137M sodium chloride with an overall pH of 7.4 at 25° C. After sterilization, the solution was ready for use.

1.1.5 Physiological Water

Physiological water was used, containing 4.25 g NaCl (Carl Roth GmbH, Karlsruhe, Germany) for 500 mL of sterile distilled water. Before use, the solution was sterilized at 121° C. for 30 min.

1.2 Selection of Bacteria

During the experiment, the following bacteria were used:
  *Staphylococcus epidermidis*
  *Acinetobacter lwoffii*
  *Propionibacterium acnes* (*Cutibacterium acnes*)
  *Enhydrobacter aerosaccus*
  *Corynebacterium tuberculostearicum*
  *Corynebacterium amycolatum*
  *Staphylococcus hominis*
  *Enterobacter cloacae*
  *Micrococcus luteus*

All these bacteria were stored in a −80° C. freezer with the cryoprotectant glycerol. The first four bacteria are known to be beneficial according to axillary malodor, the next seven are malodor-producing bacteria. The selected microorganisms can be obtained by any suitable manner known in the art. For example, the selected microorganism(s) may be isolated from a natural environment (e.g., the underarm skin of a person or the worn clothes or a person) or purchased from a suitable commercial source such as the American Type Culture Collection (ATCC) (10801 University Boulevard, Manassas, VA 20110 USA) or LM-UGent (BCCM/LMG Bacteria Collection, Karel Lodewijk Ledeganckstraat 35, 9000 Gent, Belgium). *Corynebacterium tuberculostearicum* TVK048 (similar to ATCC 35692), *Corynebacterium amycolatum* TVK039 (similar to ATCC 700207), and *Micro-*

*coccus luteus* TVK014 (similar to ATCC 4698) originate from human armpits, were rated by a human odor panel and assigned as malodorous. The odor panel was trained and selected and samples were rated as previously described (18). The odor panel rated the odors based on the hedonic value, which is the pleasantness of the odor—on a scale from −8 (very unpleasant) to 0 (neutral) to +8 (very pleasant), and the intensity of the odor, which is the quantity of the odor—on a scale from 0 (no odor) to +10 (very strong/intolerable). *Acinetobacter lwoffii* spp. EDM025 (similar to ATCC 15309), *Propionibacterium acnes* (*Cutibacterium acnes*) EDM035 (similar to ATCC 6919) and *Staphylococcus hominis* EDM024 (similar to ATCC 25615) originate from worn clothes samples but can also originate from the above-mentioned culture collections. *Staphylococcus epidermidis* LMG 10273, *Enhydrobacter aerosaccus* LMG 21877 and *Enterobacter cloacae* LMG 2783 originate from human samples and were obtained from the culture collection of LM-UGent. Collectively, this selection of bacteria is a good representation of the underarm microbiome and the microbiome of the bacteria living on clothes in the underarm region (16). A person skilled in the art can verify the identity of the bacterial species by verifying the hypervariable region of the 16S rRNA gene. The 16SrRNA gene of the used species is shown below:

```
Staphylococcus epidermidis
                              (SEQ ID NO: 1)
TCCTCTGACGTTAGCGGCGGACGGGTGAGTAACAC

GTGGATAACCTACCTATAAGACTGGGATAACTTCG

GGAAACCGGAGCTAATACCGGATAATATATTGAAC

CGCATGGTTCAATAGTGAAAGACGGTTTTGCTGTC

ACTTATAGATGGATCCGCGCCGCATTAGCTAGTTG

GTAAGGTAACGGCTTACCAAGGCAACGATGCGTAG

CCGACCTGAGAGGGTGATCGGCCACACTGGAACTG

AGACACGGTCCAGACTCCTACGGGAGGCAGCAGTA

GGGAATCTTCCGCAATGGGCGAAAGCCTGACGGAG

CAACGCCGCGTGAGTGATGAAGGTCTTCGGATCGT

AAAACTCTGTTATTAGGGAAGAACAAATGTGTAAG

TAACTATGCACGTCTTGACGGTACCTAATCAGAAA

GCCACGGCTAACTACGTGCCAGCAGCCGCGGTAAT

ACGTAGGTGGCAAGCGTTATCCGGAATTATTGGGC

GTAAAGCGCGCGTAGGCGGTTTTTTAAGTCTGATG

TGAAAGCCCACGGCTCAACCGTGGAGGGTCATTGG

AAACTGGAAAACTTGAGTGCAGAAGAGGAAAGTGG

AATTCCATGTGTAGCGGTGAAATGCGCAGAGATAT

GGAGGAACACCAGTGGCGAAGGCGACTTTCTGGTC

TGTAACTGACGCTGATGTGCGAAAGCGTGGGGATC

AAACAGGATTAGATACCCTGGTAGTCCACGCCGTA

AACGATGAGTGCTAAGTGTTAGGGGGTTTCCGCCC

CTTAGTGCTGCAGCTAACGCATTAAGCACTCCGCC
```

```
TGGGGAGTACGACCGCAAGGTTGAAACTCAAAGGA

ATTGACGGGGACCCGCACAAGCGGTGGAGCATGTG

GTTTAATTCGAAGCAACGCGAAGAACCTTACCAAA

TCTTGACATCCTCTGACCCCTCTAGAGATAGAGTT

TTCCCCTTCGGGGGACAGAGTGACAGGTGGTGCAT

GGTTGTCGTCAGCTCGTGTCGTGAGATGTTGGGTT

AAGTCCCGCAACGAGCGCAACCCTTAAGCTTAGTT

GCCATCATTAAGTTGGGCACTCTAAGTTGACTGCC

GGTGACAAACCGGAAGAAAGGTGGGG

Acinetobacter lwoffii
                              (SEQ ID NO: 2)
TGGGGTAAAGGCCTACCAAGGCGACGATCTGTAGC

GGGTCTGAGAGGATGATCCGCCACACTGGGACTGA

GACACGGCCCAGACTCCTACGGGAGGCAGCAGTGG

GGAATATTGGACAATGGGGGAACCCTGATCCAGC

CATGCCGCGTGTGTGAAGAAGGCCTTTTGGTTGTA

AAGCACTTTAAGCGAGGAGGAGGCTACCGAGATTA

ATACTCTTGGATAGTGGACGTTACTCGCAGAATAA

GCACCGGCTAACTCTGTGCCAGCAGCCGCGGTAAT

ACAGAGGGTGCAAGCGTTAATCGGATTTACTGGGC

GTAAAGCGCGCGTAGGTGGCCAATTAAGTCAAATG

TGAAATCCCCGAGCTTAACTTGGGAATTGCATTCG

ATACTGGTTGGCTAGAGTATGGGAGAGGATGGTAG

AATTCCAGGTGTAGCGGTGAAATGCGTAGAGATCT

GGAGGAATACCGATGGCGAAGGCAGCCATCTGGCC

TAATACTGACACTGAGGTGCGAAAGCATGGGGAGC

AAACAGGATTAGATACCCTGGTAGTCCATGCCGTA

AACGATGTCTACTAGCCGTTGGGGCCTTTGAGGCT

TTAGTGGCGCAGCTAACGCGATAAGTAGACCGCCT

GGGGAGTACGGTCGCAAGACTAAAACTCAAATGAA

TTGACGGGGGCCCGCACAAGCGGTGGAGCATGTGG

TTTAATTCGATGCAACGCGAAGAACCTTACCTGGT

CTTGACATAGTAAGAACTTTCCAGAGATGGATTGG

TGCCTTCGGGAACTTACATACAGGTGCTGCATGGC

TGTCGTCAGCTCGTGTCGTGAGATGTTGGGTTAAG

TCCCGCAACGAGCGCAACCCTTTTCCTTATTTGCC

AGCGGGTTAAGCCGGGAACTTTAAGGATACTGCCA

GTGACAAACTGGAGGAAGGCGGGGACGACGTCAAG

TCATCATGGCCCTTACGACCAGGGCTACACACGTG

CTACAATGGTCGGTACAAAG
```

*Propionibacterium acnes*
*(Cutibacterium acnes)*
(SEQ ID NO: 3)
GGTAGCCGGCCTGAGAGGGTGACCGGCCACATTGG

GACTGAGATACGGCCCAGACTCCTACGGGAGGCAG

CAGTGGGGAATATTGCACAATGGGCGGAAGCCTGA

TGCAGCAACGCCGCGTGCGGGATGACGGCCTTCGG

GTTGTAAACCGCTTTCGCCTGTGACCAAGCGTGAG

TGACGGTAATGGGTAAAGAAGCACCGGCTAACTAC

GTGCCAGCAGCCGCGGTGATACGCAGGGTGCGAGC

GTTGTCCGGATTTATTGGGCGTAAAGGGCTCGTAG

GTGGTTGATCGCGTCGGAAGTGTAATCTTGGGGCT

TAACCCTGAGCGTGCTTTCGATACGGGTTGACTTG

AGGAAGGTAGGGGAGAATGGAATTCCTGGTGGAGC

GGTGGAATGCGCAGATATCAGGAGGAACACCAGTG

GCGAAGGCGGTTCTCTGGGCCTTTCCTGACGCTGA

GGAGCGAAAGCGTGGGGAGCGAACAGGCTTAGATA

CCCTGGTAGTCCACGCTGTAAACGGTGGGTACTAG

GCGTGGGGTCCATTCCACCGGGTTCCGTGGCCGTA

GCTAACGCTTCAAGTACCCCGCCTGGGGAGTACGG

CCGCAAGGCTAAAACTCAAAGGAATTGACGGGGCC

CCGCACAAGCGGCGGAGCATGCGGATTAATTAGAT

GCCACGCCTAGAACCTTACCTGGGCTTGACACGGA

TCGGGAGTGCTCAGAGATGGGTGTGCGCTCTTTTG

GGGTCGGTTCACAGGCGGTGCATGGCTGTCGTCAG

CTCGTGTCGTGAGATGTTGGGATAAGTCCCGCAAC

GAGCGCAACCCTTCTTCCCTGCTGCCAGCACGTTA

TGGCGGGG

*Enhydrobacter aerosaccus*
(SEQ ID NO: 4)
CCGGACTCCTACGGGAGGCAGCAGTGGGGAATATT

GGACAATGGGGGCAACCCTGATCCAGCCATGCCGC

GTGTGTGAAGAAGGCCTTTTGGTTGTAAAGCACTT

TAAGCAGGGAGGAGAGGCTAATGGTTAATACCCAT

TAGATTAGACGTTACCTGCAGAATAAGCACCGGCT

AACTCTGTGCCAGCAGCCGCGGTAATACAGAGGGT

GCGAGCGTTAATCGGAATTACTGGGCGTAAAGCGA

GTGTAGGTGGCTCATTAAGTCACATGTGAAATCCC

CGGGCTTAACCTGGGAACTGCATGTGATACTGGTG

GTGCTAGAATATGTGAGAGGGAAGTAGAATTCCAG

GTGTAGCGGTGAAATGCGTAGAGATCTGGAGGAAT

ACCGATGGCGAAGGCAGCTTCCTGGCATAATATTG

ACACTGAGATTCGAAAGCGTGGGTAGCAAACAGGA

TTAGATACCCTGGTAGTCCACGCCGTAAACGATGT

CTACTAGCCGTTGGGGTCCTTGAGACTTTAGTGGC

GCAGTTAACGCGATAAGTAGACCGCCTGGGGAGTA

CGGCCGCAAGGTTAAAACTCAAATGAATTGACGGG

GGCCCGCACAAGCGGTGGAGCATGTGGTTTAATTC

GATGCAACGCGAAGAACCTTACCTGGTGCTATGAC

TCATAGCTGAGAATGCTGCTGCAGAGATGAGAGAG

TGCCTTCGGGAACTCACATACAGGTGCTGCATGGC

TGTCGTCAGCTCGTGTCGTGAGATGTTGGGTTAAG

TCCCGCAACGAGCGCAACCCTTTTC

*Corynebacterium tuberculostearicum*
(SEQ ID NO: 5)
CGGGTGAGTAACACGTGGGTGATCTGCCCTGCACT

TCGGGATAAGCC

TGGGAAACTGGGTCTAATACCGGATAGGAGCCATT

TTTAGTGTGATGGTTGGAAAGTTTTTTCGGTGTAG

GATGAGCTCGCGGCCTATCAGCTTGTTGGTGGGGT

AATGGCCTACCAAGGCGGCGACGGGTAGCCGGCCT

GAGAGGGTGGACGGCCACATTGGGACTGAGATACG

GCCCAGACTCCTACGGGAGGCAGCAGTGGGGAATA

TTGCACAATGGGCGCAAGCCTGATGCAGCGACGCC

GCGTGGGGGATGACGGCCTTCGGGTTGTAAACTCC

TTTCGCTAGGGACGAAGCTTTTTGTGACGGTACCT

AGATAAAAAGCACCGGCTAACTACGTGCCAGCAGC

CGCGGTAATACGTAGGGTGCGAGCGTTGTCCGGAA

TTACTGGGCGTAAAGGGCTCGTAGGTGGTTTGTCG

CGTCGTCTGTGAAATTCCGGGGCTTAACTCCGGGC

GTGCAGGCGATACGGCCATAACTTGAGTACTGTAG

GGGTAACTGGAATTCCTGGGGTAGCGCTGAAATGC

GCAGATATCAGGAGGAACACCGATGGCGAAGGCAG

GTTACTGGGCAGTTACTGACGCTGAGAAGCGAAAG

*Corynebacterium amycolatum*
(SEQ ID NO: 6)
GTGGCGAACGGGTGAGTAACACGTGGGTGACCTGC

CCTGCACTTCGGGATAAGCCTGGGAAACTGGGTCT

AATACCGGATAGGACCGCACCGTGAGGGTGTGGTG

GAAAGTTTTTCGGTGTGGGATGGGCCCGCGGCCT

ATCAGCTTGTTGGTGGGGTAATGGCCTACCAAGGC

GGCGACGGGTAGCCGGCCTGAGAGGGTGGACGGCC

ACATTGGGACTGAGACACGGCCCAGACTCCTACGG

GAGGCAGCAGTGGGGAATATTGCACAATGGGCGGA

AGCCTGATGCAGCGACGCCGCGTGGGGGATGACGG

-continued
```
CCTTCGGGTTGTAAACTCCTTTCACCATCGACGAA

GGGTTTCTGACGGTAGATGGAGAAGAAGCACCGG

TAACTACGTGCCAGCAGCCGCGGTAATACGTAGGG

TGCGAGCGTTGTCCGGAATTACTGGGCGTAAAGAG

CTCGTAGGTGGTTTGTCGCGTCGTCTGTGAAATTC

CGGGGCTTAACTCCGGGCGTGCAGGCGATACGGGC

ATAACTTGAGTACTGTAGGGGAGACTGGAATTCCT

GGTGTAGCGGTGAAATGCGCAGATATCAGGAGGAA

CACCGGTGGCGAAGGCGGGTCTCTGGGCAGTAACT

GACGCTGAGGAGCGAAAGCATGGGGAGCGAACAGG

ATTAGATACCCTGGTAGTCCATGCCGTAAACGGTG

GGCGCTAGGTGTGGGTTTCCTTCCACGGGATCCGT

GCCGTAGCTAACGCATTAAGCGCCCCGCCTGGGGA

GTACGCCGCAAGGCTAAAACTCAAAGGAATTGAC

GGGGGCCCGCACAAGCGGCGGAGCATGTGGATTAA

TTCGATGCAACGCGAAGAACCTTACCTGGGCTTGA

CATATACAGGATCGCGCCAGAGATGGTGTTTCCCT

TGTGGCTTGTATACAGGTGGTGCATGGTTGTCGTC

AGCTCGTGTCGTGAGATGTTGGGTTAAGTCCCGCA

ACGAGCGCAACCCTTGTCTTATGTTGCCAGCACGT

TGTGGTGGGGACTCGTAAAGAAACTGCCCGGGGT

TAAC
```

*Staphylococcus hominis*
(SEQ ID NO: 7)
```
GTTAGCGGCGGACGGGTGAGTAACACGTAGGTAAC

CTACCTATAAGACTGGGATAACTTCGGGAAACCGG

AGCTAATACCGGATAATATTTCGAACCGCATGGTT

CGATAGTGAAAGATGGCTTTGCTATCACTTATAGA

TGGACCTGCGCCGTATTAGCTAGTTGGTAAGGTAA

CGGCTTACCAAGGCAACGATACGTAGCCGACCTGA

GAGGGTGATCGGCCACACTGGAACTGAGACACGGT

CCAGACTCCTACGGGAGGCAGCAGTAGGGAATCTT

CCGCAATGGGCGAAAGCCTGACGGAGCAACGCCGC

GTGAGTGATGAAGGTCTTCGGATCGTAAAACTCTG

TTATTAGGGAAGAACAAACGTGTAAGTAACTGTGC

ACGTCTTGACGGTACCTAATCAGAAAGCCACGGCT

AACTACGTGCCAGCAGCCGCGGTAATACGTAGGTG

GCAAGCGTTATCCGGAATTATTGGGCGTAAAGCGC

GCGTAGGCGGTTTTTTAAGTCTGATGTGAAAGCCC

ACGGCTCAACCGTGGAGGGTCATTGGAAACTGGAA

AACTTGAGTGCAGAAGAGGAAAGTGGAATTCCTGG

TGTAGCGGTGAAATGCGCAGAGATATGGAGGAACA
```

-continued
```
CCAGTGGCGAAGGCGACTTTCTGGTCTGTAACTGA

CGCTGATGTGCGAAAGCGTGGGGATCAAACAGGAT

TAGATACCCTGGTAGTCCACGCCGTAAACGATGAG

TGCTAAGTGTTAAGGGGGTTTCCGCCCCTTAGTGC

TGCAGCTAACGCATTAAGCACTCCGCCTGGGGAGT

ACGACCGCAAGGTTGAAACTCAAAGGAATTGACGG

GGACCCGCACAAGCGGTGGAGCATGTGGTTTAATT

CGAAGCAACGCGAAGAACCTTACCAAATCTTGACA

TCCTTTGACCCTTCTAGAAGATAGAAGTTTCCCCT

TCGGGGGACAAAGTGACAGGTGGTGCATGGTTGTC

GTCAGCTCGTGTCGTGAGATGTTTGGGTTAAGTCC

CGCAACGAGCGCAACCCTTAAGCTTAGTTGCCATC

ATTAAGTTGGGCACTCTAAGTTGACTGCCGGT
```

*Enterobacter cloacae*
(SEQ ID NO: 8)
```
GAGTGGCGGACGGGTGAGTAATGTCTGGGAAACTG

CCTGATGGAGGGGGATAACTACTGGAAACGGTAGC

TAATACCGCATAATGTCGCAAGACCAAAGAGGGGG

ACCTTCGGGCCTCTTGCCATCAGATGTGCCCAGAT

GGGATTAGCTAGTAGGTGGGGTAACGGCTCACCTA

GGCGACGATCCCTAGCTGGTCTGAGAGGATGACCA

GCCACACTGGAACTGAGACACGGTCCAGACTCCTA

CGGGAGGCAGCAGTGGGGAATATTGCACAATGGGC

GCAAGCCTGATGCAGCCATGCCGCGTGTATGAAGA

AGGCCTTCGGGTTGTAAAGTACTTTCAGCGGGGAG

GAAGGTGTTGTGGTTAATAACCGCAGCAATTGACG

TTACCCGCAGAAGAAGCACCGGCTAACTCCGTGCC

AGCAGCCGCGGTAATACGGAGGGTGCAAGCGTTAA

TCGGAATTACTGGGCGTAAAGCGCACGCAGGCGGT

CTGTCAAGTCGGATGTGAAATCCCCGGGCTCAACC

TGGGAACTGCATTCGAAACTGGCAGGCTGGAGTCT

TGTAGAGGGGGGTAGAATT
```

*Micrococcus luteus*
(SEQ ID NO: 9)
```
GGGTGAGTAACACGTGAGTAACCTGCCCTTAACTC

TGGGATAAGCCTGGGAAACTGGGTCTAATACCGGA

TAGGAGCGCCCACCGCATGGTGGGTGTTGGAAAGA

TTTATCGGTTTTGGATGGACTCGCGGCCTATCAGC

TTGTTGGTGAGGTAATGGCTCACCAAGGCGACGAC

GGGTAGCCGGCCTGAGAGGGTGACCGGCCACACTG

GGACTGAGACACGGCCCAGACTCCTACGGGAGGCA

GCAGTGGGGAATATTGCACAATGGGCGAAAGCCTG
```

```
                      -continued
ATGCAGCGACGCCGCGTGAGGGATGACGGCCTTCG

GGTTGTAAACCTCTTTCAGTAGGGAAGAAGCGAAA

GTGACGGTACCTGCAGAAGAAGCACCGGCTAACTA

CGTGCCAGCAGCCGCGGTAATACGTAGGGTGCGAG

CGTTATCCGGAATTATTGGGCGTAAAGAGCTCGTA

GGCGGTTTGTCGCGTCTGTCGTGAAAGTCCGGGGC

TTAACCCCGGATCTGCGGTGGGTACGGGCAGACTA

GAGTGCAGTAGGGGAGACTGGAATTCCTGGTGTAG

CGGTGGAATGCGCAGATATCAGGAGGAACACCGAT

GGCGAAGGCAGGTCTCTGGGCTGTAACTGACGCTG

AGGAGCGAAAGCATGGGGAGCGAACAGGATTAGAT

ACCCTGGTAGTCCATGCCGTAAACGTTGGGCACTA

GGTGTGGGGACCATTCCACGGTTTCCGCGCCGCAG

CTAACGCATTAAGTGCCCCGCCTGGGGAGTACGGC

CGCAAGGCTAAAACTCAAAGGAATTGACGGGGGCC

CGCACAAGCGGCGGAGCATGCGGATTAATTCGATG

CAACGCGAAAGAACCTTACCAAGGCTTGACATGTT

CTCGATCGCCGT
```

Bacteria were grown until plateau phase before conducting in vitro tests. A bacterium, stored in the −80° C. freezer, was defrosted and spread with a Drigalski spatula on an ACX-agar plate. This plate was incubated for 24 hours at 37° C. Afterwards, a colony was picked up from the medium and brought to a new ACX-plate by using the streak plate method. After 24 h of incubation, a pure strain was brought into a 10 mL tube with sterile nutrient broth. After 24 h, the bacterium was ready for use. Growth curves of each selected strain was performed to check for exponential, plateau and decay phase. This was done measuring the maximal optical density (ODmax) using a spectrophotometer.

1.3 In Vitro Experiments
1.3.1 Biolog Plates

Phenotype microarray multiwell plates were filled with a series of acids and used to screen for potentially interesting acids increasing the growth of Staphylococcus epidermidis and other good-odor associated bacteria, versus decreasing the growth of malodor-associated bacteria. The microarray plates were inoculated with a fresh culture of the most prevalent underarm bacteria and incubated for 24 h. Before, during and after that period, the growth was measures with a spectrophotometer. Incubation and measurement was also conducted for 48 h. Measurements per compound was done in triplicate and the average of each measurement was used in downstream analyses.

Results
Experiment 1: Screening of 48 Acid Compounds

Phenotype microarray multiwell plates were assembled with a series of acids and used to screen for interesting compounds. Incubation occurred at 37° C. for 24 h and 48 h. Results of the growth/inhibition of the good odor-associated bacteria relative to malodor-associated bacteria are presented in FIG. 1. In the first phase, selection of interesting compounds occurs based on the following parameters:

Sum of growth/inhibition of beneficial deducted with the sum of growth/inhibition of detrimental bacteria Ability to lead to extra growth of S. epidermidis
Ability to inhibit Corynebacterium spp.
Ability to create extra growth of beneficial bacteria as compared to the detrimental bacteria In the second phase, selection of interesting compounds occurs based on the following parameters (Table 1):
Price
Color
Odor
Toxicity for humans/mammals.

Interesting compounds are listed in column "Compound" if good-odorous bacteria are increased in abundance and malodor-associated bacteria are not (significantly) increased or decreased in growth. The toxicity for human use (on skin) is checked as well as its odor, color and its price. The toxicity is indicated with "−" if it is toxic, irritant, or both for humans or on skin; if not toxic or irritant a "+" is assigned. Prices were looked up with Sigma-Aldrich and/or Alibaba. For odor, a "=" is assigned if no odor is present, a "−" is assigned if it has a bad smell, and a "+" is assigned if it has a good odor. Information that is not available is indicated with NA. From the 48 acids, about 25 acids were withheld as interesting compounds (Table 1).

TABLE 1

Interesting compounds after 24 h of incubation at 37° C. for phenotype microarray plates. The toxicity, price (2018), odor and color of the compound is checked.

| Compound | Toxicity | Price (€/kg) or (€/L) | Odor | Color |
|---|---|---|---|---|
| Gallic acid | + | 10 | = | white |
| Tricarballylic acid | + | 4000 | NA | beige |
| L-lactic acid | + | 42 | = | colorless |
| Fumaric acid | + | 10 | = | white |
| Mucic acid | + | 380 | = | white |
| Citric acid | + | 1 | = | white |
| D,L-Malic acid | + | 6 | = | white |
| Stearic acid | + | 3 | = | white |
| γ-Aminobutyric acid | + | 8 | = | white |
| α-Keto-glutaric acid | + | 483 | = | light yellow |
| Acetic acid | + | 1 | = | colorless |
| Quinic acid | + | 1475 | = | white |
| D-saccharic acid | + | 5500 | = | white |
| Glyoxylic acid | + | 780 | NA | light yellow |
| D-glucosaminic acid | + | 10000 | = | white |
| 4-hydroxybenzoic acid | + | 100 | = | colorless |
| N-acetyl-neuraminic acid | + | 12000 | NA | white |
| β-hydroxybutyric acid | + | 8000 | NA | white |
| Orotic acid | +− | 3500 | = | colorless |
| ε-Amino-N-caproic acid | + | 560 | = | colorless |
| Ferulic acid | + | 100 | = | white |
| Tropic acid | + | 50 | = | white |
| Hippuric acid | + | 90 | = | white |
| D,L-α-amino-caprylic acid | + | 10000 | = | white |
| D,L-α-amino-N-butyric acid | + | 8000 | = | white |

REFERENCES

1. Makin S A, Lowry M R. Deodorant Ingredients. In: K Laden, editor Antiperspirants and deodorants. New York: Marcel Dekker; 1999. p. 169-214.
2. Boonme P, Songkro S. Antiperspirants and Deodorants: Active Ingredients and. 2010; (01):5-10.
3. Callewaert C, Hutapea P, Van de Wiele T, Boon N. Deodorants and antiperspirants affect the axillary bacterial community. Arch Dermatol Res. 2014 Sep. 19; 306 (8):701-10.

4. Bouslimani A, Silva R, Amir A, Kosciolek T, Janssen S, Dorrestein K, et al. Modifying skin metabolome and microbiome with personal care products. Manuscript in preparation. 2017;
5. James A G, Casey J, Hyliands D, Mycock G. Fatty acid metabolism by cutaneous bacteria and its role in axillary malodour. World J Microbiol Biotechnol. 2004; 20(8): 787-93.
6. James A G, Austin C J, Cox D S, Taylor D, Calvert R. Microbiological and biochemical origins of human axillary odour. FEMS Microbiol Ecol. 2013; 83(3):527-40.
7. Zeng X N, Leyden J J, Lawley H J, Sawano K, Nohara I, Preti G. Analysis of characteristic odors from human male axillae. J Chem Ecol. 1991; 17(7):1469-92.
8. Natsch A, Gfeller H, Gygax P, Schmid J, Acuna G. A specific bacterial aminoacylase cleaves odorant precursors secreted in the human axilla. J Biol Chem. 2003; 278(8):5718-27.
9. Natsch A, Derrer S, Flachsmann F, Schmid J. A broad diversity of volatile carboxylic acids, released by a bacterial aminoacylase from axilla secretions, as candidate molecules for the determination of human-body odor type. Chem Biodivers. 2006; 3(1):1-20.
10. Hasegawa Y, Yabuki M, Matsukane M. Identification of new odoriferous compounds in human axillary sweat. Chem Biodivers. 2004; 1(12):2042-50.
11. Natsch A, Schmid J, Flachsmann F. Identification of odoriferous sulfanylalkanols in human axilla secretions and their formation through cleavage of cysteine precursors by a C-S lyase isolated from axilla bacteria. Chem Biodivers. 2004; 1(7):1058-72.
12. Troccaz M, Starkenmann C, Niclass Y, van de Waal M, Clark A J. 3-methyl-3-sulfanylhexan-1-ol as a major descriptor for the human axilla-sweat odour profile. Chem Biodivers. 2004; 1(7):1022-35.
13. Chen Z-S, Guo Y, Belinsky M G, Kotova E, Kruh G D. Transport of bile acids, sulfated steroids, estradiol 17-beta-D-glucuronide, and leukotriene C4 by human multidrug resistance protein 8 (ABCC11). Mol Pharmacol. 2005 February; 67(2):545-57.
14. Decréau R A, Marson C M, Smith K E, Behan J M. Production of malodorous steroids from androsta-5,16-dienes and androsta-4,16-dienes by Corynebacteria and other human axillary bacteria. J Steriod Biochem Mol Biol. 2003; 87:327-36.
15. Casey J, Ellis J E, James A G, Taylor G M. Method of reducing or preventing malodour. WO2000001353A1, 1998. p. 1-25.
16. Callewaert C, Kerckhof F M, Granitsiotis M S, van Gele M, van de Wiele T, Boon N. Characterization of *Staphylococcus* and *Corynebacterium* Clusters in the Human Axillary Region. PLoS One. 2013 Aug. 12; 8(8).
17. Atlas R. Handbook of Microbiological Media, Fourth Edition. 2010.
18. Callewaert C, De Maeseneire E, Van de Wiele T, Boon N. Bacterial and odor profile of polyester and cotton clothes after a fitness session. Commun Agric Appl Biol Sci. 2013; 78(1).

The invention claimed is:

1. A method of selectively promoting on skin or a textile growth, metabolism, and/or colonization of good-odor associated bacteria selected from the group consisting of *Staphylococcus epidermidis, Acinetobacter* spp, *Propionibacterium acnes* and *Enhydrobacter aerosaccus* bacteria, and/or selectively inhibiting on skin or a textile the growth, metabolism, and/or colonization of malodor-associated bacteria comprising *Corynebacterium tuberculostearicum, Corynebacterium amycolatum, Staphylococcus hominis, Micrococcus luteus*, or *Enterobacter cloacae*, the method comprising:
   administering or applying to the skin or textile a composition comprising an acid selected from the group consisting of, fumaric acid, mucic acid, γ-aminobutyric acid, α-keto-glutaric acid, quinic acid, D-saccharic acid, glyoxylic acid, D-glucosaminic acid, D,L-α-amino-caprylic acid, N-acetyl-neuraminic acid, D,L-α-amino-N-butyric acid, orotic acid, ε-amino-N-caproic acid, β-hydroxybutyric acid, tropic acid, hippuric acid, and any combination thereof.

2. The method according to claim 1, wherein the acid selected is fumaric acid.

3. The method according to claim 1, wherein the acid selected is mucic acid.

4. The method according to claim 1, wherein the acid selected is γ-aminobutyric acid.

5. The method according to claim 1, wherein the acid selected is α-keto-glutaric acid.

6. The method according to claim 1, wherein the acid selected is quinic acid.

7. The method according to claim 1, wherein the acid selected is D-saccharic acid.

8. The method according to claim 1, wherein the acid selected is glyoxylic acid.

9. The method according to claim 1, wherein the acid selected is D-glucosaminic acid.

10. The method according to claim 1, wherein the acid selected is D,L-α-amino-caprylic acid.

11. The method according to claim 1, wherein the acid selected is N-acetyl-neuraminic acid.

12. The method according to claim 1, wherein the acid selected is D,L-α-amino-N-butyric acid.

13. The method according to claim 1, wherein the acid selected is orotic acid.

14. The method according to claim 1, wherein the acid selected is ε-amino-N-caproic acid.

15. The method according to claim 1, wherein the acid selected is β-hydroxybutyric acid.

16. The method according to claim 1, wherein the acid selected is tropic acid.

17. The method according to claim 1, wherein the acid selected is hippuric acid.

* * * * *

UNITED STATES PATENT AND TRADEMARK OFFICE
CERTIFICATE OF CORRECTION

PATENT NO. : 12,226,503 B2
APPLICATION NO. : 17/605418
DATED : February 18, 2025
INVENTOR(S) : Chris Callewaert Page 1 of 1

It is certified that error appears in the above-identified patent and that said Letters Patent is hereby corrected as shown below:

In the Specification

Column 2, Line 17, change "Na-acyl-glutamine" to --$N^{\alpha}$-acyl-glutamine--

Column 5, Lines 1-12, change " 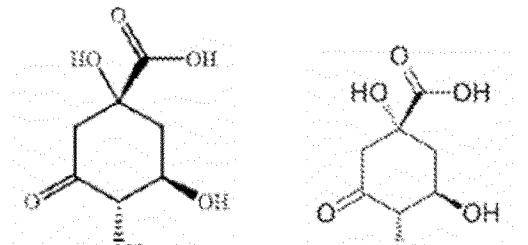 " to -- --

Column 5, Lines 35-40, change " 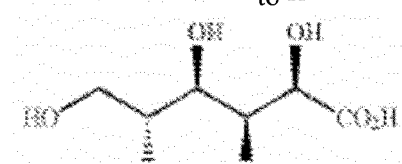 " to -- 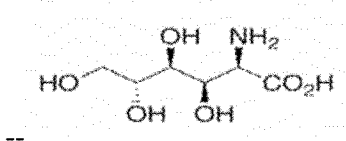 --

Column 10, Line 21, change "110 g/L CaCl$_2$) were" to --110 g/L CaCl$_2$ were--

Column 10, Lines 26-27, change "0.1 mL CaCl$_2$) solution." to --0.1 m/L CaCl$_2$ solution.--

In the Claims
Claim 1, Column 29, Lines 12-13, change "or textile a composition" to --or textile composition--

Claim 1, Column 29, Line 14, change "consisting of, fumaric acid," to --consisting of fumaric acid,--

Signed and Sealed this
Thirteenth Day of May, 2025

Coke Morgan Stewart
*Acting Director of the United States Patent and Trademark Office*